United States Patent [19]

Fleming et al.

[11] Patent Number: 4,962,022

[45] Date of Patent: Oct. 9, 1990

[54] STORAGE AND USE OF LIPOSOMES

[75] Inventors: Beverly M. Fleming; James P. Mapes, both of Raleigh, N.C.

[73] Assignee: Becton Dickinson and Company, Franklin Lakes, N.J.

[21] Appl. No.: 910,413

[22] Filed: Sep. 22, 1986

[51] Int. Cl.$^5$ ............... G01N 33/53; G01N 33/543; A01N 25/26; A61K 37/22

[52] U.S. Cl. .................... 435/7; 424/417; 424/450; 436/501; 436/518; 436/534; 436/536; 436/826; 436/829

[58] Field of Search .............. 424/450, 415, 417; 435/7, 810; 436/535, 829, 826, 501, 518, 534, 536; 8/638, 647, 650, 652

[56] References Cited

U.S. PATENT DOCUMENTS

| | | | |
|---|---|---|---|
| 4,483,929 | 11/1984 | Szoka | 436/548 |
| 4,522,803 | 6/1985 | Lenk et al. | 436/829 |
| 4,668,638 | 5/1987 | Janoff et al. | 436/829 |
| 4,695,554 | 9/1987 | O'Connell et al. | 436/501 |
| 4,731,210 | 3/1988 | Weder et al. | 436/829 |
| 4,736,018 | 4/1988 | Reutelingsperger | 514/21 |

FOREIGN PATENT DOCUMENTS

| | | | |
|---|---|---|---|
| 2538907 | 7/1984 | France | 435/7 |
| 0123459 | 7/1983 | Japan | 435/7 |
| 0138464 | 7/1985 | Japan | 435/7 |
| 8301571 | 5/1983 | PCT Int'l Appl. | 436/518 |
| 8500664 | 2/1985 | PCT Int'l Appl. | 435/7 |

Primary Examiner—Esther L. Kepplinger
Assistant Examiner—Florina B. Hoffer
Attorney, Agent, or Firm—Elliot M. Olstein; John G. Gilfillan; John N. Bain

[57] ABSTRACT

The invention relates to liposome compositions comprising liposomes in an aqueous buffer at a pH of 6.5–8.5 and including a polyol in an amount of from 0.6 to 1.5 g per 100 ml of buffer. Also, the invention further relates to liposome compositions comprising a liposome including a detectable marker wherein said liposome may be derivatized with a ligand and the use thereof in an assay for analyte of interest.

19 Claims, No Drawings

STORAGE AND USE OF LIPOSOMES

This invention relates to liposomes, and more particularly to the storage and use of liposomes in assay systems.

Vesicles or sacs are generally produced from amphiphilic compounds (compounds having both a hydrophobic portion and a hydrophilic (polar) portion), with such vesicles or sacs being most commonly produced from lipids, in particular, phospholipids. When the vesicles or sacs are produced from lipids or lipidlike materials they are most often referred to as liposomes.

In some cases, liposomes have been formed in a manner such as to encapsulate a material in the interior of the liposome. Thus, for example, such liposomes have been used to encapsulate biologically active materials; for example, a therapeutic drug.

In addition, liposomes have been employed to encapsulate a detectable marker for use in an assay for a ligand. In some cases, such liposomes, including a detectable marker, are conjugated to a ligand, and liposome including conjugated ligand and detectable marker are employed as a tracer in an assay for a ligand to be determined (analyte).

Liposomes are generally known to be relatively unstable when stored over a period of time. Thus, for example, such instability may be evidenced by either leaking of material from the interior of the liposome and/or in the case where the liposome is employed as a tracer for an assay, breaking of the bond which conjugates the ligand to the liposome.

In addition, in using the liposomes in an assay system for determining analyte, in many cases, premature leaking of encapsulated detectable marker from the liposome may produce erroneous assay results.

Accordingly, there is a need for improving the stability of liposomes to storage and/or for use in assay systems for determining analytes.

In accordance with an aspect of the present invention, the stability of liposomes is improved by providing a composition in which the liposome is in an aqueous buffer, with the aqueous buffer being buffered to a pH of from 6.5 to 8.5, and preferably from 6.5 to 8.0, and with the aqueous buffer further including a polyol (in particular, glycerol) in an amount of from 0.6 g. to 1.5 g., and preferably from 0.8 g. to 1.2 g. per 100 ml. of buffer.

Applicant has found that the storage stability of liposomes is improved by storing the liposomes in an aqueous buffer as hereinabove described. Moreover, applicant has found that when the liposomes are employed in an assay system; for example, as a tracer, by using the liposomes in a buffer as hereinabove described, such buffer is compatible with the assay system and improves the stability of the liposomes in the assay system. Furthermore, the liposomes in the storage buffer may be used in the assay without the necessity of diluting the buffered liposomes prior to use.

The pH of the buffer is maintained by employing a buffering agent which is capable of maintaining the desired pH, and which does not adversely affect the liposomes. As representative examples of suitable buffering agents, there may be mentioned: 3-[N-Morpholino]-2-hydroxypropane sulfonic acid, Piperazine-N,N'-BIS[2-ethane sulfonic acid], 2-[(2-Amino-2-oxoethyl)-Amino] ethane sulfonic acid, N,N'-BIS [2-Hydroxy-Ethyl]-2-amino ethane - sulfonic acid, sodium phosphate, tris buffer, etc.

The selection of a suitable buffer is deemed to be within the scope of those skilled in the art from the teachings herein.

In addition to the buffering agent, the storage buffer includes a polyol. The polyol preferably has a molecular weight of no greater than 1500 and is most preferably a hydrocarbon polyol. Glycerine is particularly preferred.

In addition to the buffering agent to maintain the required pH, and the glycerol, the aqueous buffer may include other materials which are conventionally employed in buffering solutions. Thus, for example, the buffer may include suitable metal chelators, proteins, salts, and antimicrobials. For example, the preferred buffer includes metal chelators such as ethylene diamine tetraacetic acid (EDTA) and ethylene glycol bis (beta amino ethyl ether)-N,N,N', N'-tetra acetic acid (EGTA). These may function to reduce the concentrations of heavy metal ions which are known to catalyze oxidation processes. The buffer also includes proteins like bovine serum albumin (BSA) or gelatin which may stabilize the liposomes from osmotic changes and help stabilize functional groups on the surface of the liposomes. The buffer may further include antimicrobial agents like sodium azide, penicillin, or gentamycin.

In accordance with a particularly preferred embodiment, the liposomes are stored in an aqueous buffer which includes as a buffering agent 3-(N-morpholino)-2-hydroxy-propane sulfonic acid (MOPSO) in an amount to provide a pH of from 6.5 to 7.3; a chelating agent, in particular ethylenediamine tetra acetic acid (EDTA) in an amount from 0.5 to 2mM; an antimicrobial agent such as sodium azide in an amount from 0.01 to 0.03 g. per 100 ml of buffer; glycerol in an amount from 0.6 to 1.5 g. per 100 ml of buffer; and a protein, in particular, bovine serum albumin in an amount from 0.05 to 0.5 g. per 100 ml of buffer.

The liposomes which are employed and/or stored in an aqueous buffer, as hereinabove described, may be prepared from a wide variety of lipids, including phospholipids, glycol lipids, and as representative examples there may be mentioned lecithin, spingomyelin, dipalmitoyl lecithin, distearoylphosphatidylcholine, etc. The amphiphilic lipids employed for producing liposomes generally have a hydrophilic group, such as a phosphoryl, carboxylic, sulfonyl, or amino group, and a hydrophobic group, such as saturated and unsaturated aliphatic hydrocarbons, and aliphatic hydrocarbon groups substituted by one or more aromatic or cycloaliphatic groups. The wall forming compounds for producing the liposomes may further include a steroid component such as cholesterol, cholestanol, and the like. The compounds for producing liposomes are generally known in the art, and no further details in this respect are deemed necessary for a complete understanding of the present invention.

The liposomes may be produced by procedures generally available in the art. For example, liposomes may be produced by a reverse phase evaporation technique wherein the compound or compounds used in producing liposomes are initially dissolved in an organic phase, followed by addition of an aqueous phase and forming of a homogeneous emulsion. After forming the emulsion, the organic solvent is evaporated to form a gel like material, and such gel may be converted to a liposome by agitation or dispersion in an aqueous media, such as a buffer solution of the types hereinabove described.

Procedures for producing liposomes are described, for example, in U. S. Pat. No. 4,241,046; U. S. Pat. No. 4,342,826 and PCT International Publication No. WO 80-01515.

If a material is to be encapsulated in the liposome, such material may be encapsulated in the liposome by including the material in the aqueous solution in which the liposome is formed. Alternatively, the material may be encapsulated into a previously formed empty liposome (without material to be encapsulated) by the procedure described in U. S. application Ser. No. 659,200, filed on Sept. 13, 1984.

The liposomes may also be produced by the procedures disclosed in U. S. Pat. No. 4,522,803.

The material which is entrapped or encapsulated within the liposome (the material is within the aqueous compartment or within the membrane bilayer of the liposome)may be any one of a wide variety of materials, including detectable markers, such as dyes, radiolabels, fluorescent materials, chemiluminescent materials, electron spin resonance materials, and the like; various therapeutic agents; substrates for detectable markers; and the like. Alternatively, the detectable marker may be conjugated to the liposomes.

Liposomes having a material entrapped therein are generally known in the art, and may be stored and/or used in an aqueous buffer in accordance with the present invention. Further description of such liposomes is not deemed necessary for a complete understanding of the present invention.

In some cases, the liposome with or without a detectable marker, particularly where used as a tracer in an assay, are derivatized with a ligand. The liposome may be derivatized with a ligand by procedures known in the art, such as covalent coupling, derivatization or activation, etc. In derivatizing the liposomes with a ligand, a compound or compounds used in forming the liposome may be derivatized with the ligand, prior to forming the liposome, or alternatively the liposome may be derivatized with the ligand, subsequent to forming of the liposome. Procedures for derivatizing liposomes with ligands, and suitable coupling agents, and the like for preparing derivatized liposomes are known in the art, and no further details in this respect are deemed necessary for a complete understanding of the present invention.

In accordance with another aspect of the present invention, the liposome contains a detectable marker, and is derivatized with a ligand and employed in an assay for an analyte, in a buffer as hereinabove described. Applicant has found that liposomes, when employed in such a buffer, are compatible with assay systems, and provide for improved stability of the liposomes in such systems.

The ligand which is employed for derivatizing the liposome is dependent upon the analyte which is to be assayed. Thus, for example, if the assay is a competitive assay for determining an antigen or hapten, the ligand employed in producing the tracer would be either the analyte or appropriate analog thereof. (The term "appropriate analog" means that the analog of the analyte is bound by the binder for the analyte).

If the assay is a "sandwich" type of assay, then the ligand employed in producing the tracer would be a ligand which is specific for the analyte to be assayed; for example, an antibody for the ligand to be assayed, or if the analyte is an antibody, either an antibody or an antigen.

Thus, as should be apparent, the ligand which is employed for derivatizing the liposomes which are to be used in an assay in a buffer of the type hereinabove described may be either an antigen, a hapten, or an antibody.

The binder which is used in the assay is also dependent upon the analyte. Thus, for example, if the analyte is an antigen or hapten, the binder may be an antibody or naturally occurring substance which is specific for the analyte. If the analyte is an antibody, the binder may be either an antibody, an antigen or naturally occurring substance which is specific for the analyte.

As known in the art, the binder may be employed in supported or unsupported form, and when supported, the support material may be any one of a wide variety of materials which are known to be suitable as supports in a solid phase assay.

Thus, in accordance with the present invention, a liposome including a detectable marker (encapsulated in or conjugated to the liposome, preferably encapsulated in the liposome), and which may be derivatized with a ligand, is employed in an assay in a buffer of the type hereinabove described. As should be apparent, the scope of the present invention is not limited to a specific assay or a specific detectable marker or a specific ligand for derivatizing the liposomes in that the present invention is directed to a wide variety of such components, provided that the liposome is employed in the assay in a buffer of the type hereinabove described.

In accordance with a particularly preferred embodiment, the tracer for the assay is comprised of a liposome containing a detectable marker, which is preferably a chromogen such as sulforhodamine B, and which is derivatized with a ligand, and which is employed in a buffer as hereinabove described so as to improve the stability of the liposome in the assay.

As a representative assay, which is a competitive assay, the tracer in the buffer of the type hereinabove described is analyte or appropriate analog thereof conjugated to a liposome, which includes in the interior thereof a detectable marker, and which is contacted with both the sample containing analyte, and binder for the analyte so that the analyte and tracer compete for binding sites on the binder. The contacting may be accomplished in a simultaneous manner or in a sequential manner as known in the art.

If the assay is a non-homogeneous assay, then the "bound" and "free" phases are separated from each other, and the amount of tracer in at least one of the bound and free phases is determined as a measure of analyte. If the assay is a homogeneous assay, then it is not necessary to effect separation of the bound and free phases.

In general, the marker included in the liposome is detected by releasing the marker from the liposome; for example, by lysing of the liposome by procedures known in the art. As representative examples of such lysing agents, there may be mentioned enzymes, suitable surfactants, and the like.

The amount determined in either the bound and/or free phase is then compared with a standard curve by procedures known in the art.

Although an assay has been described with respect to a competitive type of assay, it is to be understood that the assay may also be a sandwich type of assay as known in the art. In a sandwich assay, there is provided a binder on a solid support, which is specific for the analyte, and as a tracer, a liposome containing a detectable marker, and which is derivatized with a binder which is specific for the analyte, with such tracer being employed in a buffer as hereinabove described In the assay, the analyte is contacted with both the supported binder and the tracer, either in a simultaneous procedure or a sequential procedure, as known in the art.

After separation of the bound and free phases, the amount of tracer in at least one of the bound and free phases is determined as a measure of analyte. As in a competitive assay, such determined amount is compared with a standard curve.

In accordance with still another aspect of the present invention, there is provided a reagent kit in which there is included in a suitable reagent package, a tracer comprised of a liposome including a detectable marker, which may or may not be derivatized with a ligand, and which is stored in a buffer as hereinabove described for use in an assay. The kit would further include a binder for at least one of the analyte and the ligand which is employed for derivatizing the liposome in the case where the tracer is a derivatized liposome. The reagent package or kit may further include standards (samples containing known quantities of the analyte), other buffers, and other materials which are generally employed in reagent kits. The various components may be included in the reagent package or kit in separate containers or vials.

The invention will be further described with respect to the following examples:

EXAMPLE 1

818 mg. of dipalmitoyl phosphatidylcholine (DPPE) are reacted with 428 mg of 3-ketodigoxigenin in dichloromethane/methanol (9/1, by vol) under a nitrogen atmosphere. After stirring for 3 hours at 62° C., the reactants are reduced by adding 86 mg of sodium cyanoborohydride and leaving this overnight at room temperature. The product is purified on a silica gel column and eluted with a low-pressure solvent gradient (methanol/methylene chloride, 9/1 to 8/1 by vol). The identity of the material, which yielded a single spot on thin-layer chromatography, was confirmed by NMR.

EXAMPLE 2

132 umole cholesterol, 119 umole distearoyl phosphatidylcholine, 13.2 umole distearoyl phosphatidylglycerol, and 2 umole of the preparation of Example 1 are placed in a 250 ml capacity round-bottom flask, complete to 20 ml with chloroform-methanol (9:1 v/v), and heated to 55° C. for one minute. The solvents are evaporated using a rotary evaporator at 37° C.

The flask is placed in dessicator and connected to a high vacuum for 16 hours. To this flask is added 20 ml of Dye (sulforhodamine B) solution buffer, and swirled gently in a water bath at 60 degrees C for 3 minutes. It is cooled immediately on ice. The dye-liposome suspension is extruded through polycarbonate membranes of 1.0 um and 0.4 um at 25° C. The solution is heated to 60° C and extruded twice through a 0.2 um membrane and incubated at 60° C. for 1 minute. The liposomes are cooled immediately on ice. The liposomes are diluted with standard stock buffer to 50–60 ml, and centrifuged at 100,000 xg, 4° C., for 30 minutes. The supernatant is decanted and the pellet is resuspended in 50–60 ml standard stock buffer and centrifuged again. After one more wash the pellet is resuspended at a final concentration of 1mM phosphorus/ml in standard stock buffer. The standard stock buffer is 20 mM MOPSO; 1mM EDTA; 0.02% (w/v) Sodium Azide; 1.0% (w/v) Glycerol; pH 6.7; 0.8% (w/v) BSA; and OSM 310. The dye buffer is 0.1M Sulforhodamine B, 1mM EDTA, 0.02% Sodium Azide, pH 6.7 and 310 m OSM.

EXAMPLE 3

Assay Procedure: The stock liposomes of Example 2 are diluted 20-fold in MOPSO buffer containing 1mM EDTA; 0.02% Azide; 1.0% glycerol; 0.08% BSA; 310 m OSM and the pH adjusted to 6.7. After placing 50 ul of the appropriate serum standard, test control, or test sample in an antibody coated tube, 1 mL of the prediluted digoxigenin-liposomes is added, vortex-mixed briefly; and the tubes are incubated at 37° C. for 30 minutes. The contents are decanted, inverted and blotted onto absorbent paper, rinsed with 1 mL of the liposome-diluent, and again blotted onto absorbent paper to remove any excess fluid. Finally, 850 ul of 50 mL/L Triton X-100 solution is added to each tube to lyse the bound liposomes. The absorbance of each is read in a Bausch and Lomb Spetronic 2000 spectrophotometer at 565 nm.

The present invention is particularly advantageous in that it permits effective storage of liposomes and has particular applicability to the storage and use of liposomes including a detectable marker as a tracer in an assay.

Applicant has found that, by use of the noted pH and a polyol (in particular, glycerol) in the buffer in the noted amounts, the liposomes, including a detectable marker and, preferably also derivatized with a ligand, may be stored and used in an assay, without further dilution, and without adversely affecting the assay.

Applicant has surprisingly found that low amounts of a polyol in combination with the controlled pH effectively stabilizes the liposomes.

Numerous modifications and variations of the present invention are possible in light of the above teachings and, therefore, within the scope of the appended claims, the invention may be practiced otherwise than as particularly described.

What is claimed is:

1. A composition comprising:
   an aqueous buffer and liposomes in the aqueous buffer, said aqueous buffer being at a pH of from 6.5 to 8.5, and further including a polyol in an amount of from 0.6 to 1.5 g per 100 ml. of buffer.

2. The composition of claim 1 wherein the polyol has a molecular weight of no greater than 1500.

3. The composition of claim 2 wherein the polyol is a hydrocarbon polyol.

4. The composition of claim 3 wherein the liposomes include a detectable marker.

5. The composition of claim 1 wherein the polyol is glycerol.

6. The composition of claim 1 wherein the buffer further includes a protein in an amount of from 0.5 to 0.5g per 100ml of buffer.

7. The composition of claim 6 wherein the buffer further includes a chelating agent in an amount of from 0.5 to 2M.

8. The composition of claim 1 wherein the pH is maintained by 3-(N-morpholino)-2-hydroxy-propane sulfonic acid, the polyol is glycerol and the buffer further contains a chelating agent in an amount of from 0.5 to 2mM, an antimicrobial agent in an amount of from 0.01 to 0.03 g. per 100ml of buffer, and protein in an amount of from 0.05 to 0.5 g. per 100 ml of buffer.

9. A tracer composition for use in an assay for an analyte, comprising:
a liposome including a detectable marker, said liposome being derivatized with a ligand, said liposome being in an aqueous buffer maintained at a pH of from 6.5 to 8.5, said aqueous buffer including a polyol in an amount of from 0.6 to 1.5 g. per 100 ml of buffer.

10. The composition of claim 9 wherein the polyol has a molecular weight of no greater than 1500.

11. The composition of claim 10 wherein the polyol is a hydrocarbon polyol.

12. The composition of claim 11 wherein the polyol is glycerol.

13. The composition of claim 12 wherein the detectable marker is a chromogen.

14. The composition of claim 13 wherein the chromogen is sulforhodamine B.

15. The composition of claim 13 wherein the buffer includes a chelating agent in an amount of from 0.5 to 2mM and a protein in an amount of from 0.05 to 0.5g per 100ml of buffer.

16. The composition of claim 13 wherein the pH is maintained by 3-(N-morpholino)-2-hydroxy-propane sulfonic acid, the polyol is glycerol and the buffer further contains a chelating agent in an amount of from 0.5 to 2 mM, an antimicrobial agent in an amount of from 0.01 to 0.3 g. per 100 ml of buffer, and protein in an amount of from 0.05 to 0.5 g. per 100 ml -of buffer.

17. The composition of claim 16 wherein the protein is bovine serum albumin.

18. An assay for an analyte, comprising:
contacting the tracer composition of claim 9 with a sample containing analyte to be determined and a binder for the analyte to form a free and bound tracer phase; and
determining at least one of the free and bound tracer phase to detect analyte.

19. An assay for an analyte, comprising:
contacting the tracer composition of claim 15 with a sample containing analyte to be determined and a binder for the analyte to form a free and bound tracer phase; and
determining at least one of the free and bound tracer phase to detect analyte.

* * * * *